United States Patent [19]

Schentag et al.

[11] Patent Number: 5,279,607

[45] Date of Patent: Jan. 18, 1994

[54] TELEMETRY CAPSULE AND PROCESS

[75] Inventors: Jerome J. Schentag, Eggertsville; David T. D'Andrea, Amherst, both of N.Y.

[73] Assignees: The State University of New York, Albany; Gastrotarget Corp., Tonawanda, both of N.Y.

[21] Appl. No.: 707,842

[22] Filed: May 30, 1991

[51] Int. Cl.$^5$ .............................................. A61K 9/22
[52] U.S. Cl. ................................ 604/890.1; 604/93; 604/114; 604/891.1
[58] Field of Search ............... 128/630, 631, 654, 655, 128/737, 903; 600/2, 3, 7; 604/93, 113, 145, 67, 891.1, 892.1, 890.1

[56] References Cited

U.S. PATENT DOCUMENTS

| | | | |
|---|---|---|---|
| 3,212,496 | 10/1965 | Praston | 128/631 |
| 3,659,600 | 5/1972 | Merrill | 604/93 |
| 3,893,111 | 7/1975 | Cotter | 128/631 |
| 3,923,060 | 12/1975 | Ellinwood, Jr. | 128/DIG. 13 |
| 4,146,029 | 3/1979 | Ellinwood, Jr. | 604/891.1 |
| 4,262,632 | 4/1981 | Hanton et al. | 128/631 |
| 4,373,527 | 2/1983 | Fischell | 604/891.1 |
| 4,425,117 | 1/1984 | Hugemann et al. | 604/93 |
| 4,439,197 | 3/1984 | Honda et al | 128/655 |
| 4,447,224 | 5/1984 | DeCant, Jr. et al. | 604/67 |
| 4,507,115 | 3/1985 | Kambara et al. | 604/93 |
| 4,564,363 | 1/1986 | Bagnall et al. | 604/93 |
| 4,844,076 | 7/1989 | Lesho et al. | 128/631 |

FOREIGN PATENT DOCUMENTS 3809482  10/1989  Fed. Rep. of Germany ...... 604/145

OTHER PUBLICATIONS

European Journal of Clinical Pharmacology, vol. 30, pp. 691–697.
Gut, 1960, 1, 266, Wireless Telemetering from the Digestive Tract J. Biomed., Eng. 1982, vol. 4, Jul., pp. 247–251.
The American Journal of Medicine, Nov. 30, 1989, vol. 87 (Sup. 5A) pp. 66S–69S.
Biotelemetry Patient Monitg 8:213–227 (1981).
The Heidelberg Capsule Used For the Diagnosis of Peptic Diseases, by H. G. Noller, M.D.
Aerospace Medicine, Feb. 1964, pp. 115–117.
Science, vol. 156, Apr. 21, 1967, pp. 351–360, Implant Biotelemetry and Microelectronics.
Physiology and Behavior, 1970, vol. 5, pp. 709–712.
Med. Klin. 59(1964) Nr. 16, pp. 663–666.
Electroenceph. clin. Neurophysiol., 1967, 22:275–277.
Aerospace Medicine, May 1968, pp. 488–492.
IEEE Transactions on Bio-Medical Engineering, vol. BME-14, No. 4, Oct. 1967, pp. 230–238.
Electroenceph. Clin. Neurophysiol., 1974, 37, pp. 153–160.
Dtsch. med. Wschr., 85, Jg., Nr39, Sep. 23, 1960, pp. 1707–1713.
Biotelemetry 1: 50–59 (1974).
Biotelemetry 1: 60–64 (1974).
Biotelemetry 1: 41–49 (1974).
Biotelemetry 1:31–40 (1974).
Proceedings of the Physiological Society, Apr. 1969, pp. 5P–6P.
Psychophysiology, vol. 11, No. 3, May 1974, pp. 382–387.
Minerva Medica—390, pp. 3705–3708.
Elektro Medizin 7:230–235, 1962.
Medical Research Engineering, Mar./Apr. 1969, pp. 9–15.

*Primary Examiner*—C. Fred Rosenbaum
*Assistant Examiner*—Manual Mendez
*Attorney, Agent, or Firm*—Bean, Kauffman & Spencer

[57] ABSTRACT

An ingestible capsule and process for delivery, particularly repeatable delivery, of a medicament to the alimentary canal is disclosed wherein an essentially non-digestible capsule contains an electric energy emitting means, a radio signal transmitting means, a medicament storage means and a remote actuatable medicament releasing means. The capsule signals a remote receiver as it progresses through the alimentary tract in a previously mapped route and upon reaching a specified site is remotely triggered to release a dosage of medicament.

55 Claims, 4 Drawing Sheets

TELEMETRY CAPSULE AND PROCESS

FIELD OF THE INVENTION

This application relates to a novel capsule and process for its use in the precise delivery and telemetric release of medicaments in the alimentary canal of animals, particularly humans.

BACKGROUND OF THE INVENTION

There has been a continuing need for a non-invasive means for the precise delivery of medicaments to selected sites in the animal alimentary canal. Generally, such delivery has taken the form of time delivery capsules, wherein a capsule containing the medicament is manufactured from a material that dissolves in a particular specific environment and/or within a particular time period within the alimentary canal; or, the form of elaborate mechanical devices that can be inserted into the alimentary canal by means of a mechanical tether or the like and can release the medicament at the desired location.

In dissolving type timed delivery capsule systems, the delivery of the medicament is highly dependent upon the predictability of the particular environment to which the capsule containing the medicament is subjected and nuances such as folds in the intestine, positions of the stomach which may create disruptions in passage of the capsule and the like. Dissolving type timed delivery capsules are widely used, but generally, because of the unpredictability of alimentary canal environment and the disruption of capsule passage caused by the geography of the canal, such capsules are seen as most useful for non-precise release of medicaments in general areas of the canal and are not seen as representing viable means for delivery to a specific site. Rarely are such means used when the release is intended to be limited to a specific site in the canal, such as at a particular tumor or the like.

Mechanical devices, are generally preferred when the release of the medicament is desired to occur at a specific site. Generally the mechanical devices which are used for such delivery are awkward implements, typically comprising long invasive needles or flexible tube mechanisms which are inserted into the alimentary canal with medicament release means at the inserted end. Flexible devices are typically "snaked" into the alimentary tract through the mouth, nose or anal opening and generally require anesthetizing procedures to be acceptable to the animal being treated. Release of the medicament at a specific site in the tract requires significant skill and typically must be done by a highly skilled physician using elaborate locating means such as miniaturized video, fluoroscopic, X-ray apparatus or the like.

The medical profession has long recognized the need for more reliable means for the delivery of medicaments to specific alimentary canal sites, particularly means that might be accurately and repeatedly accomplished without confining the patient to a medical facility and without requiring the intensity of medical professional attention now required by typically available mechanical means.

In recent years, "radio pill" technology has been described wherein a capsule, containing a transmitter, has been seen by the medical profession as a possible means to monitor various body environments. It has been suggested that such pills could be implanted, ingested or otherwise placed at desirable locations in the body and could be engineered to transmit critical data to a remote receiver located outside the body. The ideal radio pill is seen as one that is small enough to be easily ingested, biologically inert, disposable and inexpensive. The transmission signal would have to be sufficiently strong to be received by a remote receiver, preferably located apart from the patient's body so that the patient would have freedom of movement, or, be small enough to be carried by the patient.

As a result of such recent perceptions, researchers from Heidelberg University developed a capsule and system for monitoring pH of the gastrointestinal tract. This capsule and system, generally known as the Heidelberg pH capsule system, comprises a capsule containing a transmitter that is sensitive to pH changes experienced within the gastrointestinal tract. The patient wears a belt, which contains an antenna for collection of transmitted signals, which in turn feeds the signals to a receiver. The receiver stores and/or records the data, generally on a graph, thus providing the medical professional with a non-invasive means to monitor pH within the alimentary canal. Geographic location is not determined using the radio signals. Though the Heidelberg capsule system does allow some freedom of movement for the patient, it requires tethering of the patient to bulky machinery and has not enjoyed widespread commercial success, probably because of the limited use for the information gathered.

Another radio pill that has been recently developed is that generally known as the Konigsberg temperature telemetry pill. The Konigsberg pill is an ingestible capsule comprising a transmitter that is sensitive to temperature changes. As with the Heidelberg capsule, signals are transmitted to a collecting antenna and then to a receiver where the data is stored and/or recorded for use by the medical professional. Again, as with the Heidelberg capsule, geographic location of the capsule is not determined using the radio signals.

Each of the Heidelberg and Konigsberg capsules have utility in the short term monitoring of pH, but neither have the ability to deliver a drug at a selected site.

An object of the present invention is to provide a capsule which is easily ingestible in an animal alimentary canal and can be remote triggered to release medicament at a specified site in the canal.

Another object of the invention is to provide a capsule that can transmit a signal to a remote receiver, sufficient to determine geographic location of the capsule within the alimentary canal.

A further object of the invention is to provide a process for the tracking of a capsule through the alimentary canal.

A still further object of the invention is to provide a process for tracking a capsule through the alimentary canal and releasing a desired dosage of medicament at a specified site within the canal.

These and other objects of the invention will become apparent from the following description of the invention.

SUMMARY OF THE INVENTION

The instant invention features an ingestible capsule having an exterior surface configured for convenient passage through the alimentary canal, said capsule comprising, an electric power source, a radio signal transmitting means, a remote actuatable activating means, medicament storage means and a medicament releasing means, encased in an essentially non-digestible outer shell.

In the system of the invention, the electric power source in the capsule, provides operating power to the transmitting means, which emits radio signals from the capsule that are collected by antennae, exterior to the human body, and fed to an appropriate remote receiver. The capsule containing such transmitter is ingested in the alimentary canal and remote antennae, typically arranged about the body of the animal, collect signals from the capsule at various intensity and direction to provide tracking information to the remote receiver. The remote receiver in turn amplifies, distinguishes and/or converts all or portions of the signals to usable data which is provided to storage and/or comparator means, typically comprising a central process unit such as a computer. The comparator, compares the data from the receiver with previously obtained data pertaining to geographic positions within the alimentary canal contained in the storage means and computes or confirms location. Upon receipt of signals from the capsule indicating alignment of the capsule at a specified site in the alimentary canal, remote means actuates the remote actuatable activating means of the capsule, which in turn actuates the medicament releasing means causing the stored medicament to be released from the capsule.

As can be seen from the aforesaid recitation, the process of the invention generally comprises obtaining directional data from the passage of a signal transmitting capsule through an alimentary canal to create a precise map of the routing of the capsule to a precise location in the canal. This directional data is stored and compared to directional data from a subsequent signal transmitting capsule or capsules carrying medicament passing through the alimentary canal at a later time. Thus, once the route has been mapped and stored, the passage of subsequent capsules can be accurately repeated and the precise release of medicament at a selected site can be accurately achieved through multiple repetitions.

The advantage of such process is particularly applicable with a patient that requires periodic application of medicament at a specific location in the gastrointestinal tract. Such patient typically receives a first exploratory treatment in a controlled office environment wherein a signal transmitting capsule is ingested and passed through the alimentary canal with its geographic route being mapped to the precise route that a medicament containing capsule would take to a specific location in the canal. The mapped route is then stored in the computer for further reference. Thereafter, treatment comprises ingestion of a medicament containing capsule, in a loosely controlled environment, and computer controlled release of the medicament from a remote triggering device at the appropriate arrival of the capsule at the desired site. Significantly, using differential signals, two or more capsules can be contained in the alimentary canal at the same time, providing means to deliver medicament to the same or different sites at the same or varying times.

BRIEF DESCRIPTION OF THE DRAWINGS

The nature and mode of operation of the present invention will now be more fully described in the following detailed description taken with the accompanying drawings wherein.

DESCRIPTION OF THE PREFERRED EMBODIMENT

Figure 1:
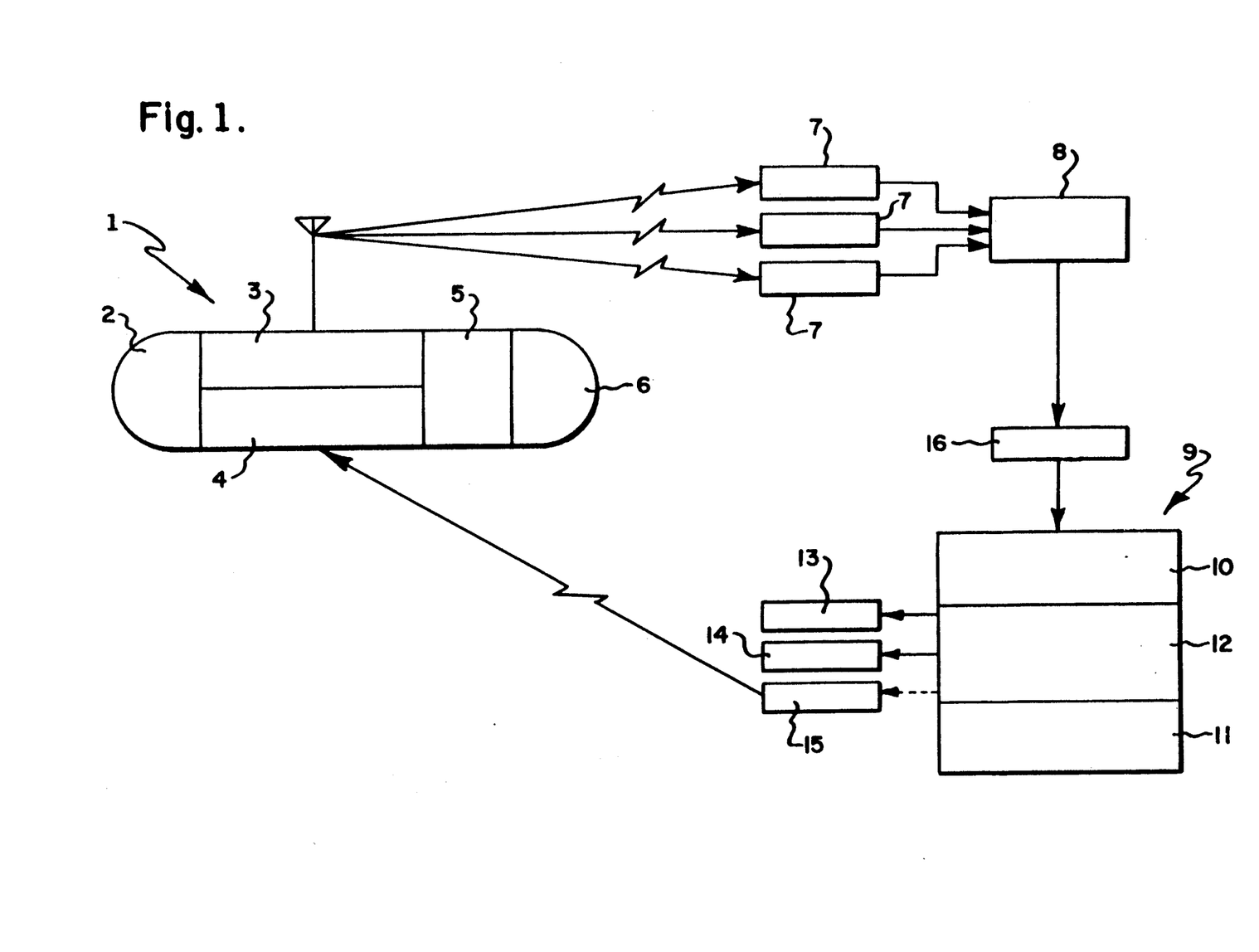
FIG. 1 is a schematic illustration of a typical system of the invention.

FIG. 1 comprises a schematic illustration of the main components of the telemetry capsule system of the invention and the manner in which they are interrelated in typical operation.

Therein, capsule 1, typically comprises an electric power source 2, radio signal transmitter 3, remote controlled actuator 4, medicament releasing assembly 5 and medicament storage compartment 6, which are interrelated to provide the two functions of transmittal of tracking data and dosage release.

In functioning to provide tracking data, transmitter 3, emits a radio signal(s) from the capsule that is collected by antennae 7, located exterior to the body, which in turn feed the signal to an appropriate remote receiver 8. Signals emitted from the transmitter are typically constant and generally need not vary in frequency, intensity or the like to provide adequate tracking data. Typically, multiple antennae are utilized in the system of the invention for collection of signals from capsule transmitting means 3 to obtain precise positioning of the capsule in the alimentary canal through geometric triangulation in combination with an expert system based software. The antennae can be located in fixed instrumentation to which the patient is confined, but, generally the multiple antennae are arranged about the body in a vest or belt type unit that allows the patient to move about in a wide range of daily activity.

A remote receiver, preferably miniaturized, is typically hard wired to the multiple antennae and receives the multiple signals collected thereby. The receiver may in turn be hard wired to one or more central processing units and non-volatile memory, or, may be in radio communication with a further receiver, which in turn is hard wired to a one or more central processing units.

Typically, the receiver/transmitter is mounted together with the antennae on the body and is hard wired to one or more central processing units which may or may not also be on the body. The signal received by the transmitter is typically amplified, differentiated or otherwise distinguished and/or converted to data which can be used in the central processing unit for determining location of the capsule emitting the signals. This data, in turn, is typically internally stored within non-volatile memory for later review and analysis.

In a further embodiment of the invention, which would allow the patient maximum freedom, a first receiver-transmitter is mounted together with the antennae on the body and is in radio communication with a second receiver that is hard wired to one or more central processing units. The signal received by the receiver, which is hard wired to the central processing unit, is processed in a similar fashion to that described above.

Central processing unit 9 generally constitutes a computer or the like, typically comprising data distribution means 10, data storage means 11 and comparator/computing means 12. Data from the remote receiver 8 is typically routed to micro-controller means 16 then to distribution means 10, wherein it is distributed to comparator/computing means 12 and/or storage means 11. Comparator/computing means 12, generally compares data received from the distribution means with previously stored data and analyzes, computes and/or confirms geometric location of the capsule within the alimentary canal. Monitor 13 and/or printer 14 is typically provided to allow visual confirmation, to the operator, of the status and location of the capsule. Micro-controller means 16 provides means for digitizing data from the antennae receiver instrumentation.

Upon receipt of signals from the capsule indicating alignment of the capsule at a specified site in the alimentary canal, the dosage release function of the capsule is typically undertaken. To initiate dosage release, remote trigger 15 transmits an actuating signal to the actuator of the capsule, which in turn actuates the medicament releasing assembly causing the stored medicament to be released from the capsule.

Figure 2:
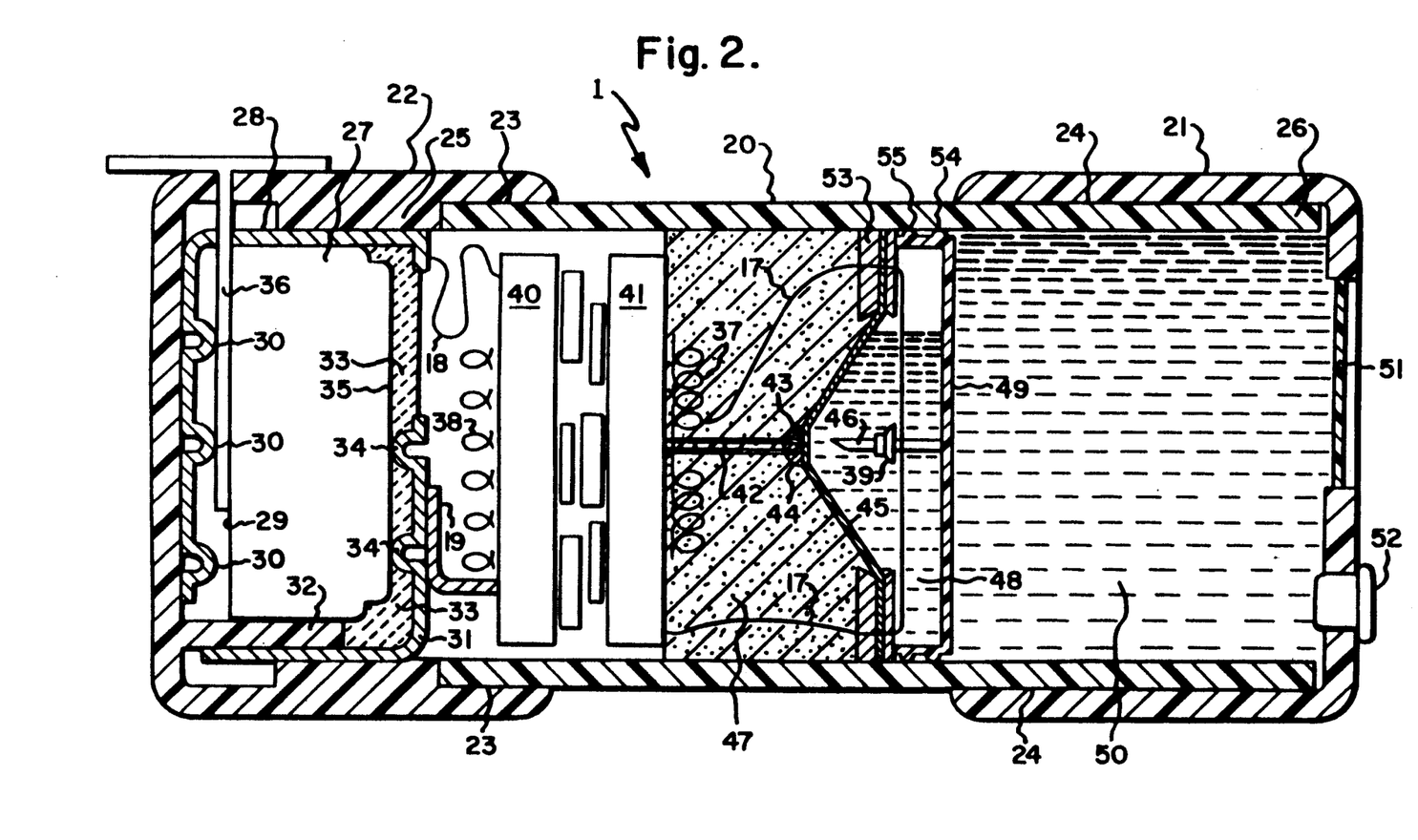
FIG. 2 is a sectional view of a typical capsule of the invention.

FIG. 2 is a sectional view of a typical capsule of the invention. Therein, capsule comprises generally cylindrical central shell 20, which typically contains the electronics and mechanical assembly, medicament end cap 21 and power source end cap 22 assembled to form a non-digestible outer capsule shell. Medicament end cap 21 comprises filling membrane 51 and dosing plug 52. Typically the end caps are sealed at 23 and 24, around central shell 20, using a non toxic glue or adhesive to prevent leakage of digestive tract fluids into the capsule and/or leakage of medicament and/or reactants out of the capsule. Barrier 25 and central shell end 26 are dimensioned to provide consistent placement, respectively, of the power source and medicament end caps.

Power source end cap 22, generally comprises a battery 27, positive bus bar 28 and negative bus bar 31. Positive bus bar 28 is in contact with the positive terminal of the battery 27 through contact points 30 and is generally in contact with the exterior rear and side walls of the battery. Interior divider 32 and sealant 33 maintain battery 27 in position and insulate negative bus bar 31 from contact with a positive side or bottom wall of the battery, while allowing negative contact at contact points 34 with the negative terminal 35 of the battery. The negative terminal 35 is typically located at a central area in the top wall of the battery.

Negative bus bar 31 is typically in closed electric contact, through connecting bar 19, with transmitter 40 and activator 41. Insulating lockout 36, is removably installed between contacts 30 of positive bus bar 28 and the positive battery terminal 29 to inactivate the circuit until use of the capsule is desired. Negative bus bar 31 is in contact with the circuitry of transmitter 40 and actuator 41. Removal of insulating lockout 36, completes an electric circuit through connecting wire 18 to transmitter 40 and actuator 41 to allow activation of actuator 41 upon receipt of an appropriate signal from the remote trigger. In the process of the invention, lockout 36 is removed just prior to ingestion of the capsule and the hole in the capsule from which it is withdrawn is closed by installing a silicon rubber plug, or with sealant or the like.

Transmitter 40 operates independently of actuator 41 and is designed to emit a detectable radio signal, from transmission coil 38, upon completion of the circuit by removal of lockout 36. The radio signal may be constant or can be intermittent, but should be of sufficient intensity to be detectable through an antenna located outside the body, by a receiver. Generally, a nonmodulated signal, outside the broadcast range, is preferred. Typically there is no provision for switching off transmitter 40 and it remains in a transmitting mode throughout passage of the capsule through the alimentary tract.

Actuator 41 typically constitutes a single function receiver, that closes a circuit to an "on" position, activating initiator coil 37, upon receipt of a defined activating transmission signal. The initiator coil typically is characterized by a detectable resonate frequency. In a preferred embodiment of the invention, once the circuit is triggered it stays in the "on" position through the remainder of the capsule's passage through the alimentary canal.

Generally, the activating transmission signal is narrowly defined to prevent inadvertent activation by stray background radio signals. Upon receipt of an appropriate signal from the remote trigger of the system, actuator 41 generally directs power from the battery through power transmission lines 42 to filament 43. The use of the battery power by the actuator generally results in rapid dissipation of the energy available from the power source and typically transmission of detectable radio signals from the capsule will decrease in intensity and eventually cease to be detectable. This decrease or cessation of detectable radio signals is typically seen as confirmation that the dosing procedure has begun.

The medicament delivery portion of the capsule generally comprises power transmission lines 42, filament 43, glue spot 44, diaphragm 45, rupture pin 46, reactant 47, reactant 48, trip wire 17 and piston 49.

Diaphragm 45 is generally circular in form and is engaged with the interior of the central shell through circumferential retainer clip 53. The diaphragm is comprised of an elastomeric material, such as silicon rubber, latex rubber or the like, that can be outwardly distended from its center without rupturing, and can form an effective barrier between the two reactants. Generally it is also desirable that the elastomeric material be such that when pierced it will tear to provide a significant rupture. Silicon rubber has been found to be an effective elastomer for use as a diaphragm, however it should be understood that any elastomer that may function as previously described is contemplated as within the invention. Power transmission lines 42 have a dual function, first in that they conduct electric current to filament 43 from actuator 41, and second in that they constitute attachment wires that extend from the actuator to the diaphragm, with sufficient tensile strength to hold the diaphragm in a distended position. The attachment wires are held to the diaphragm by thermal sensitive glue spot 44.

Various thermal sensitive glues may be used in the invention, though a preferred thermal sensitive glue can be formed by mixing raw polymethylpentene plastic stock with a satiable solvent such as tetrahydrofuran, methylethylketone or the like, with cyclohexanone to form a paste which, when hardened, will have the desired thermal characteristics.

When filament 43 receives current from actuator 41, through transmission lines 42, it heats the thermal sensitive glue of glue spot 44 and causes the glue to soften and release the diaphragm from attachment to transmission lines 42. Generally, filament 43 comprises a tungsten or the like filament that will generate heat upon imposing a current therethrough. Upon release, the distended elastomeric diaphragm moves toward its normal generally straight position across the capsule. As the diaphragm moves toward its normal generally straight position it engages rupture pin 46 which pierces the diaphragm and causes it to rupture. Rupturing of the diaphragm allows reactant 48 to contact reactant 47 and a reaction proceeds.

Generally it is desirable that reactant 47 be a solid reactant, that reactant 48 be a liquid reactant and the reaction product be a gas. Typically, the solid reactant is a bicarbonate such as sodium bi-carbonate and the liquid is an organic acid, such as weak acetic acid, such that mixing of the two forms a gaseous reaction product. The production of the gas product must be sufficient to create pressure adequate to move piston 49 into the medicament storage compartment. Ring seals 54 and 55 are provided on piston 49 to prevent leakage of the reactants and/or gaseous product of the reaction from entering the medicament compartment.

Figure 3:
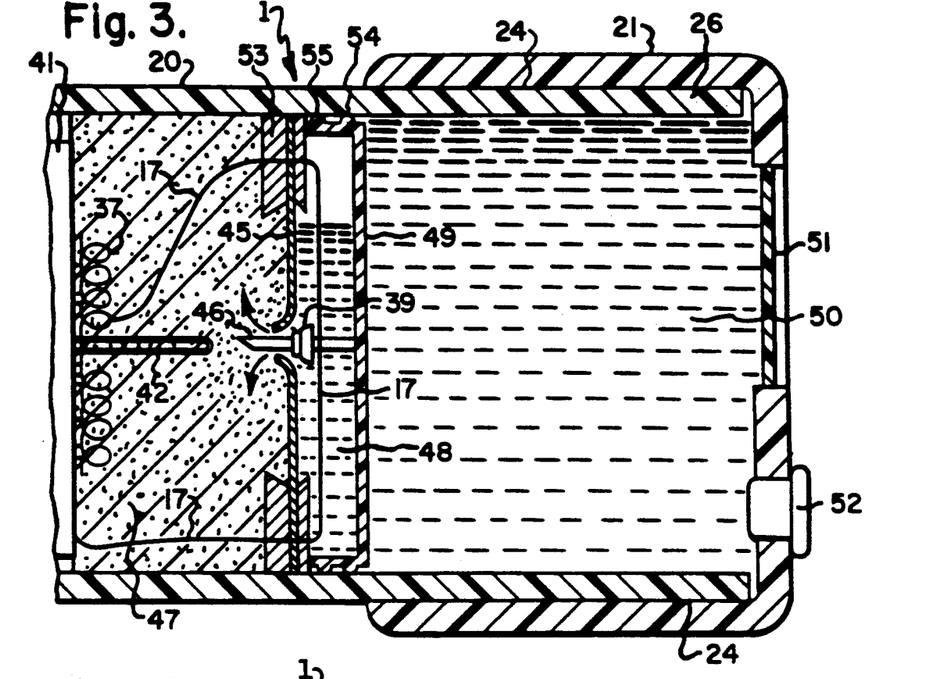
FIG. 3 is a fragmentary sectional view of the medicament and activating chambers of the capsule of FIG. 2 at activation.
Figure 4:
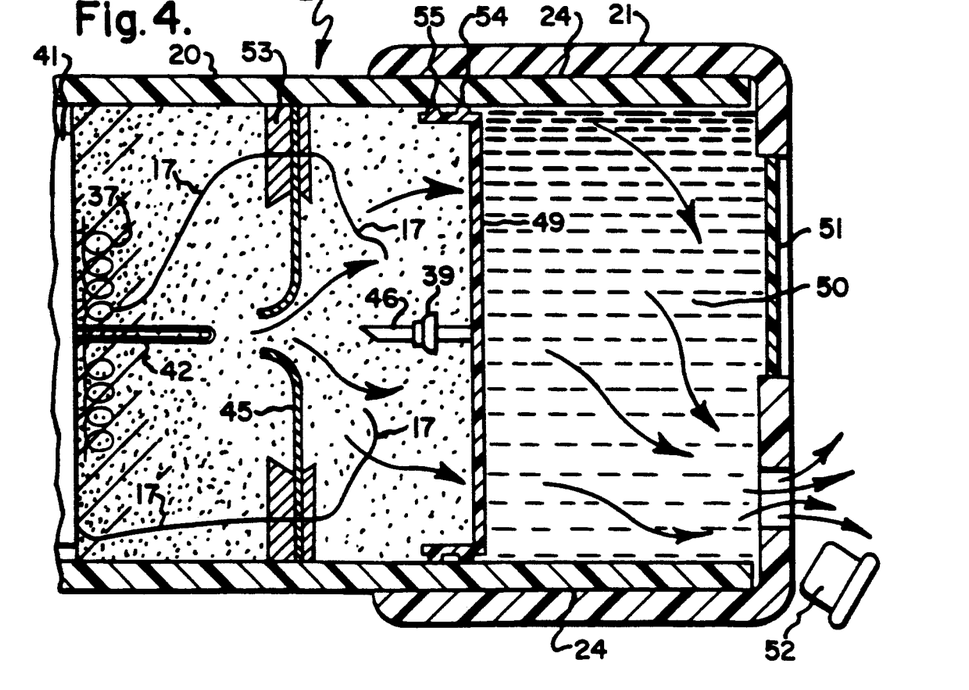
FIG. 4 is a fragmentary sectional view of the medicament and activating chambers of the capsule of FIG. 2 during dosing.

FIGS. 3 and 4 illustrate the drug delivery system of the capsule. In FIG. 3, the remote trigger has signaled the actuator which closes a circuit from the power source and imposes a current upon transmission lines 42, causing the filament 43 to heat the thermal sensitive glue spot 44. The thermal sensitive glue spot has melted, releasing diaphragm 45 to allow its return to a normal straight position. The diaphragm has been ruptured by rupture pin 46 to allow liquid reactant to move into the area holding the solid reactant and contact the solid reactant. In FIG. 4, the contacting solid and liquid reactants react and the reaction has proceeded such that sufficient gas has been generated to move piston 49 forward into the medicament storage compartment. Rupture pin 46 is mounted to piston 49, and, as it moves forward into the medicament storage compartment, the piston displaces medicament 50 with sufficient force to pop out dosing plug 52, and force the medicament out of the capsule. In addition, as the piston moves forward, barb 39 of rupture pin 46, engages trip wire 17 and causes it to break.

Trip wire 17 generally is arranged to comprise a parallel circuit with all or part of initiator coil 37 such that breaking trip wire 17 creates a detectable change in the resonate frequency of the initiator coil which can be monitored as a detectable dosing indicator signal, indicating medicament release. The length of the trip wire may be adjusted to various distances that the piston may travel before a detectable rupture of the trip wire occurs. Typically it is desirable to adjust the wire so that the detectable change in resonance frequency occurs at a piston position that confirms the completion of dosing.

Dosing plug 52 is typically comprised of a material which is generally resistant to alimentary tract fluids. Generally a silicon rubber plug is used, such that upon being expelled from the capsule it will pass harmlessly through the alimentary canal, with the capsule, after dosing has been accomplished. Typically, dosing plug 52 is fitted to the dosage release hole in the medicament end cap as a final assembly step to prevent leakage of fluids into or out of the end cap.

Filling membrane 51 is comprised of a material such as silicon rubber or the like that is generally resistant to alimentary tract fluids. Typically, filling membrane 51 covers a suitable dosage filling hole in the medicament end cap and is glued or otherwise sealed to the end cap to prevent leakage of fluids into or out of the end cap. The membrane is comprised of a material that is strong and/or thick enough to resist bursting upon being subjected to the differential in pressure created within the capsule, by the generation of gas, and is self sealing when pierced by one or more needles or the like for filling the medicament storage compartment, with or without trapped air release. Membrane materials of this nature are widely available being extensively used as filler membranes in medicament supply bottles and the like.

Figure 5:
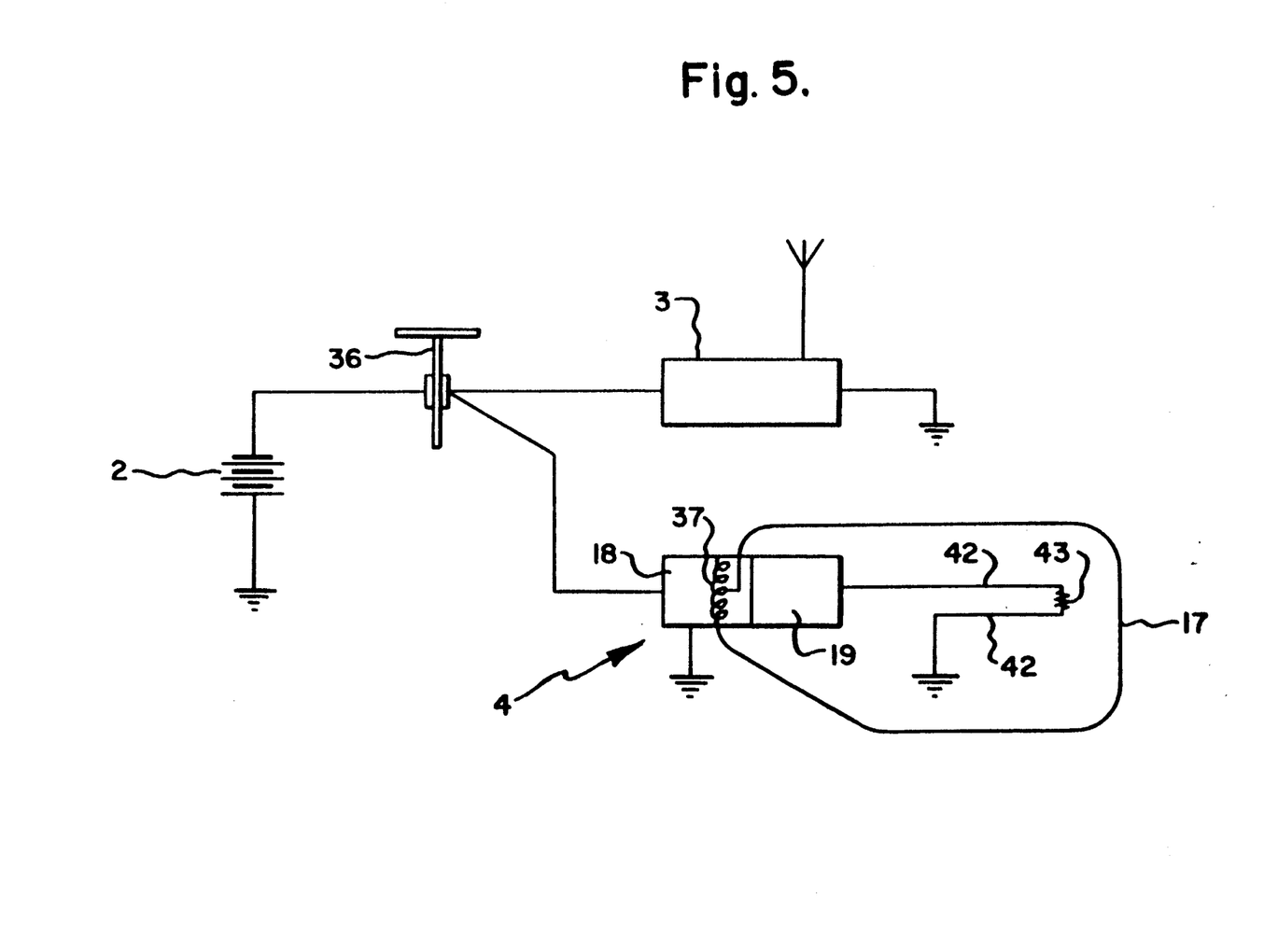
FIG. 5 is a schematic illustration of the activating system of the capsule.

FIG. 5, comprises a block diagram illustrating typical circuitry of a capsule of the invention. Therein, is illustrated that upon removal of insulating lockout 36, the circuitry of radio signal transmitting means 3 is completed and the transmitting means is powered, by electric power source 2, to begin emitting radio signals and continue same, until the power from the power source is dissipated. At the same time, receiver circuit 56 of remote controlled actuator 4 is enabled but not powered, such that upon receiving a proper signal from a remote trigger, the receiver circuit will actuate filament circuit 57. Actuation of filament circuit 57 actuates initiator coil 37, including the parallel circuit of trip wire 17, and causes current to flow through transmission lines 42 through tungsten filament 43 to ground causing the filament to heat up. It should be noted that preferably, deactivation of the transmitter circuit does not occur upon actuation of filament circuit so that the incident of capsule dosing providing a secondary indication that the incident of capsule dosing has occurred.

A wide variety of electric power sources can be used in the capsule of the instant invention. Generally, such means can comprise a storage battery or can also comprise an electric generating device that is activated during use of the capsule. Typically, modern mercury, silver oxide, NiCad and lithium batteries are suitable in size and energy storage for use in the capsule of the present invention.

Similarly, mechanical power generators might be used in the capsule of the invention, such as tensioned spring electric generating devices and the like. Such devices must be subminiature in size and the number of moving parts required reduces the probability of their widespread use. Radioisotope power sources have been suggested as electric power supply means for subminiature utilities, however such means are not yet commercially available for use.

In another embodiment of the instant invention, a chemical and/or biological fuel cell comprises the power source, such as yeast metabolites reacting with an electrode material.

Generally the capsule can be formed from any suitable material that will resist degradation from passing through the alimentary canal. Generally, a polycarbonate material is preferred for the outer shell. Various medicaments, liquid, solid or gaseous may be used with the capsule and process of the invention. Generally it is preferred to use a liquid medicament or dispersion in a liquid carrier.

Radio signal transmitting and receiving means suitable for use in the capsule of the invention are well known in the art. Sub-miniature radio transmitters as described by A. M. Connell in GUT, 1960, 1, pp 266 and H.G. Noller, in Medical Electronics, 1960, pp 342 appear suitable for the capsule of the invention.

The remote receiver and antennae are generally seen as comprising a receiver subsystem for the purposes of the invention. Typically, such receiver subsystem used in the process of the invention comprises multiple dipole antennae, the outputs of which are time multiplexed to a computer tuned superheterodyne receiver and quadrature detector.

In the general operation of a typical receiver subsystem of the invention, the output from multiple dipole antennae, typically about eight, are matched in impedance by processing through a common impedance matching network. The matched output of the antennae are then time multiplexed, by means of data input control from the computer and the multiplexed signal is channeled to a radio frequency (RF) amplifier of the receiver for amplification. The amplified signal is then channeled to the computer tuned superheterodyne receiver where it is typically filtered to remove spurious signals and then implied to an RF input of a mixer to convert it to an intermediate frequency signal for convenient processing. The intermediate frequency signal is directed to a quadrature detector that confirms received signal validity, with valid signals being then digitized by the receiver for transmittal to the computer. The intermediate frequency output of the mixer is also amplified, and applied by the receiver to an absolute value circuit to quantify signal strength as a DC voltage signal representing relative received signal strength from each antenna and is transmitted to the computer.

Receivers which can detect the presence of a valid input frequency, measure the relative strength of the signal, amplify, detect and digitize the signal are commonly available and typically used as communications receivers.

The computer subsystem generally comprises a commonly available instrument micro-controller and a typical central processing unit which includes a distribution means, comparator/computer, data storage means, monitor, printer and appropriate software.

In the general operation of the process, the digitized valid signals confirm continuing identification of the capsule and the DC voltage signal from each antenna is digitized by the micro-controller to provide capsule location input to the central processing unit. Thus as a dosing capsule moves through the alimentary canal the variations in quantified DC voltage signal, derived from each antenna and digitized by the micro-controller, are compared by the software of the central processing unit to the digitized historic DC voltage signal data obtained from the previous passage of a non-dosing capsule. In addition to the direct comparison of digitized non-dosing historic DC voltage signal data, comparison may be made with other factors such as length of time in the canal, active antennae group, historic progress rate through the canal, rate and/or time models, normalized or model voltage signal data and the like. Typically, the software scans and computes variations from the non-dosing historic signal data, together with variations from one or more other factors, in pre-programed weighted relation to establish a calculated probability of geometric location of the dosing capsule. Typically the calculated probability is continually monitored by the central processing unit and upon variation beyond pre-programed limits will scan and recalculate discarding and/or incorporating other factors as may be pre-programed into the software. Such recalculating, discarding and/or incorporating of other factors is generally referred to as the expert system of the software for purposes of this application. Typically, the software is pre-programed to signal the operator or otherwise initiate dosing when the calculated geometric location conforms to the pre-programed desired location within pre-defined limits of probability. The exceeding of such pre-defined limits of probability, even in view of scanning and recalculation, is also typically signaled to the operator to indicate failure of accurate location.

The components of the remote trigger and the release verification system remote from the capsule are generally considered the release initiator and verification subsystem for purposes of the invention. Typically such subsystem comprises an initiator coil, initiator pulse amplifier, transmit/receive (TR) switch and a release verification grid dip module in the RF receiver.

In typical operation of the process of the invention, the computer signals when initiation of medicament release is appropriate. The initiator pulse amplifier acts to shape and amplify a pulse from the initiation signal and sends it to the initiator coil, which acts as a transmitting antenna to transmit the amplified pulse to the actuator of the capsule. The TR switch is typically located before the multiplexer of the multiple dipole antennae and disconnects the multiple antennae from the multiplexer while the pulse amplifier is in operation to prevent damage to the low level circuitry of the RF receiver, particularly the grid dip module, from the high powered pulse.

After the amplified pulse has been transmitted the TR switch reconnects the antennae to the multiplexer and the grid dip module senses the resonate frequency of the activator circuit of the capsule. As the trip wire in the capsule stretches and/or breaks, the activator circuitry changes and results in a change of frequency which is also detected by the grid dip module.

Typically, the operation of the initiator pulse amplifier and TR switch are inter-controlled by the central processing unit. The data corresponding to the changes or failure to change frequency is transmitted by the receiver to the CPU and the software can be preprogrammed to re-initiate the sequence, indicate dosing success or failure, as may be desired.

While various particular embodiments of the invention have been shown and described, it will, of course be understood that various modifications can be made without departure from the principles of the invention.

We claim:

1. An ingestible capsule for delivery of a medicament to the alimentary canal of an animal comprising, an electric power source, a radio signal transmitting means in enabling circuitry with said power source suitable for transmitting a radio signal the location from which emanates being trackable through animal tissue, a medicament storage compartment, and a medicament releasing means for releasing medicament from said storage compartment, all encased in an essentially non-digestable outer shell that is configured to pass through said alimentary canal, said medicament releasing means being actuatable by radio signal transmitted from a site exterior of the body of said animal.

2. The capsule of claim 1 wherein said electric power source comprises a battery.

3. The capsule of claim 1 wherein said transmitting means emits a radio signal, detectable exterior to said outer shell of said capsule, when enabled by said power source.

4. The capsule of claim 1 wherein said medicament storage compartment comprises a dosing means and a filling means.

5. The capsule of claim 4 wherein said filling means comprises a self sealing membrane arranged to be pierced for providing medicament to said storage compartment.

6. The capsule of claim 4 wherein said dosing means comprises a removable plug arranged to be expelled from said capsule at dosing.

7. The capsule of claim 1 wherein said medicament releasing means comprises an activating means and a medicament releasing means, said activating means being arranged to initiate measurement releasing activity of said medicament releasing means.

8. The capsule of claim 7 wherein said activating means comprises an electric heating filament, in enabling circuitry with said power source.

9. The capsule of claim 1 wherein said remote actuatable medicament releasing means comprises means for receiving a radio signal from a remote transmitting means positioned exterior of said outer shell of said capsule.

10. The capsule of claim 7 wherein said activating means comprises an initiator coil, in enabling circuitry with said power source, that is characterized by emitting a detectable resonate frequency when said activating means is activated.

11. The capsule of claim 8 wherein said medicament releasing means comprises a diaphragm, arranged between reactants and separating said reactants from contacting, and said heating filament is detachably joined to said diaphragm by means of a thermal sensitive glue.

12. The capsule of claim 1 wherein said releasing means comprises a diaphragm, arranged between and separating reactants, that, upon contacting each other, will form a gas.

13. The capsule of claim 12 wherein said reactants comprise an acid and a base.

14. The capsule of claim 13 wherein said base comprises sodium bi-carbonate and said acid is an organic acid.

15. The capsule of claim 12 further comprising means to rupture said diaphragm to the extent that the separated reactants will contact.

16. The capsule of claim 15 wherein said means to rupture said diaphragm comprises a rupture pin arranged to engage said diaphragm when said diaphragm is released from a distended position.

17. The capsule of claim 16, wherein said diaphragm is held in said distended position by means comprising an electric heating filament detachably joined, by thermal sensitive glue, to said diaphragm.

18. The capsule of claim 17 wherein said means comprises enabling circuitry from said power source for conducting electricity to said filament.

19. The capsule of claim 7 wherein said medicament releasing means comprises a movable piston.

20. The capsule of claim 19 wherein said piston is adapted to cause medicament to be expelled from the capsule through movement of said piston forcing medicament stored in said medicament storage compartment to be expelled from said capsule.

21. The capsule of claim 20 comprising a trip wire arranged to be engaged upon movement of said piston.

22. The capsule of claim 20 wherein a trip wire is arranged to break with said movement of said piston.

23. The capsule of claim 21 wherein said trip wire is arranged to engage means for detecting medicament dosing.

24. The capsule of claim 23 wherein said trip wire is an electrical conductor and engages an initiator coil in parallel circuitry that is characterized by a detectable resonate frequency when activated.

25. The capsule of claim 24 wherein breaking said trip wire modifies said parallel circuitry and changes the resonate frequency of said initiator coil.

26. The capsule of claim 1 wherein said outer shell comprises a polycarbonate.

27. The capsule of claim 1 wherein said enabling circuitry comprises a switching means.

28. An ingestible capsule for delivery of a medicament to the alimentary canal comprising, a non-digestible outer shell; an electric power source; a radio signal transmitting means in enabling circuitry with said power source suitable for transmitting a radio signal the location from which is emanates being trackable through animal tissue; a medicament storage compartment comprising a filling membrane and a dosing means; and, a remote actuatable medicament releasing means.

29. An ingestible capsule for delivery of a medicament to the alimentary canal comprising, a non-digestible outer shell; an electric power source; a radio signal transmitting means in enabling circuitry with said power source suitable for transmitting a radio signal the location from which it emanates being trackable through animal tissue; a medicament storage compartment comprising a filling membrane and a dosing means; diaphragm means, arranged to separate reactants that upon contact generate a gaseous product; means to rupture said diaphragm; and piston means, arranged to move in response to generation of said gaseous product.

30. The capsule of claim 29 comprising means to receive a radio signal.

31. The capsule of claim 30 containing a medicament in said medicament storage compartment.

32. A process for the delivery of a medicament to a selected site in the alimentary canal of an animal comprising, providing an ingestible capsule containing a signal transmitting means, medicament and a remote actuatable medicament releasing means; ingesting said capsule into the alimentary canal; transmitting a signal trackable through animal tissue from said transmitting means contained in said capsule, said signal being suitable for determining location of said capsule; receiving said transmitted signal exterior of the body of said animal; comparing said signal to a pre-established model and transmitting an actuating signal to said remote actuatable medicament releasing means contained in said capsule for releasing said medicament from said capsule, in response to the comparison.

33. The process of claim 32 wherein said signal is a radio signal.

34. The process of claim 32 wherein a radio signal is transmitted from said transmitting means in said capsule and is received at multiple receiving antennae arranged about the exterior of the body of said animal.

35. The process of claim 34 wherein the output of said multiple receiving antennae is directed to time multiplexing means and said output is converted to time multiplexed output.

36. The process of claim 33 wherein said radio signal, transmitted from said transmitting means in said capsule, is converted to an intermediate frequency signal.

37. The process of claim 36 wherein an intermediate frequency signal is quantified as a DC voltage signal.

38. The process of claim 37 wherein a quantified DC voltage signal is digitized to provide input to a computer.

39. The process of claim 35 wherein said time multiplexed output of the multiple receiving antennae is converted to an intermediate frequency signal, quantified as a DC voltage signal and digitized to provide input to a computer.

40. The process of claim 32 wherein digitized information from said transmitted signal is compared to digitized information from said pre-established model in a computer.

41. The process of claim 32 wherein said pre-established model comprises historic data obtained from the previous passage of a radio signal transmitting capsule through said alimentary canal.

42. The process of claim 32 wherein said pre-established model comprises digitized information having parameters comprising one of rate of progress of said capsule through said canal, length of time of said capsule in said canal or normalized model.

43. The process of claim 32 wherein said transmitted signal is received exterior of the animal body digitized and provided to a computer.

44. The process of claim 43 wherein said pre-established model comprises digitized historic data obtained from the previous passage of a capsule through said alimentary canal.

45. The process of claim 43 wherein said pre-established model comprises digitized information having parameters comprising one of rate of progress of said capsule through said canal, length of time of said capsule in said canal or normalized model.

46. The process of claim 43 wherein said computer is programed to scan and compute variations from pre-programed factors.

47. The process of claim 43 wherein said computer is programed to initiate an actuating signal to the medicament releasing means of the capsule.

48. The process of claim 43 wherein initiation of said actuating signal is operator controlled.

49. The process of claim 32 wherein release of said medicament initiates a dosing indicator signal, by a dosing indicator signal means comprised in said capsule, which is detectable exterior of the body of said animal.

50. The process of claim 47 wherein release of said medicament initiates a dosing indicator signal, by a dosing indicator signal means comprised in said capsule, which is detectable exterior of the body of said animal.

51. The process of claim 50 wherein said computer is programed to re-initiated an actuating signal when a dosing indicator signal is not received by said computer after it has initiated an actuating signal.

52. The process of claim 32 comprising two or more capsules in the alimentary canal transmitting differential signals.

53. The process of claim 32 wherein a first ingestible capsule, containing a signal transmitting means, is ingested into said alimentary canal; a signal transmitted from said capsule is received exterior of said body and digitized in a computer; and said digitized data from a signal transmitted from said first capsule comprises said pre-established model.

54. A process for the collection of data for the delivery of a medicament to a selected site in the alimentary canal of an animal comprising, providing an ingestible capsule containing a radio signal transmitting means suitable for determining location of said capsule ingesting said capsule into the alimentary canal; transmitting a radio signal from said transmitting means; receiving said transmitted signal exterior of the body of said animal at multiple receiving antennae arranged about said canal; digitizing said signal received by said multiple antennae; storing said digitized signal in computer recoverable, time sequence memory.

55. The process of claim 54 wherein said stored digitized signal is compared to digitized data derived from transmitted signals from the passage of another capsule through said alimentary canal.

* * * * *